United States Patent [19]
Inamoto et al.

[11] 4,169,958
[45] Oct. 2, 1979

[54] 3-ALKOXY-4-HOMOISOTWISTANES

[75] Inventors: Yoshiaki Inamoto; Koji Aigami, both of Wakayama; Naotake Takaishi, Sakura; Motoki Nakajima, Miyashiro, all of Japan

[73] Assignee: Kao Soap Co., Ltd., Tokyo, Japan

[21] Appl. No.: 893,828

[22] Filed: Apr. 6, 1978

[30] Foreign Application Priority Data
Apr. 11, 1977 [JP] Japan .................. 52/40339

[51] Int. Cl.$^2$ ............................ C07C 43/00
[52] U.S. Cl. .................... 568/665; 252/522; 426/538
[58] Field of Search ............ 260/611 F; 568/665

[56] References Cited
U.S. PATENT DOCUMENTS
3,383,423  5/1968  Moore ..................... 260/611 F Primary Examiner—Bernard Helfin
Attorney, Agent, or Firm—Oblon, Fisher, Spivak, McClelland & Maier

[57] ABSTRACT

3-Alkoxy-4-homoisotwistanes the formula (I),

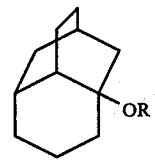

(I)

wherein R is an alkyl group having 1 to 6 carbon atoms or a cycloalkyl group having 5 to 6 carbon atoms, are prepared by a process which comprises reacting a 3-halogeno-4-homoisotwistane of the formula (II),

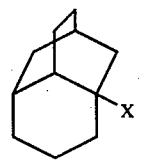

(II)

wherein X is a chlorine or bromine atom, with an alcohol of the formula (III),

R—OH          (III)

wherein R is as above defined. A perfume and flavor composition comprising, such a homotwistane possesses an excellent perfume.

2 Claims, No Drawings

3-ALKOXY-4-HOMOISOTWISTANES

BACKGROUND OF THE INVENTION

1. Field of the Invention

This invention relates to a novel tricycloundecanol derivatives, more particularly to 3-alkoxy-4-homoisotwistanes of the formula (I),

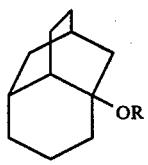
(I)

wherein R represents an alkyl group having 1 to 6 carbon atoms or a cycloalkyl group having 5 to 6 carbon atoms. The invention also relates to a process for producing 3-alkoxy-4-homoisotwistanes of the formula (I), and a novel perfume and flavor composition comprising such homoisotwistanes.

2. Description of the Prior Art

The carbon framework of the present compound, 4-homoisotwistane (tricyclo[5.3.1.0$^{3,8}$]undecane), was first synthesized by A. Kranz et al [Chem. Commun., 1387 (1971) and J. Amer. Chem. Soc., 95, 5662 (1973)]. Thereafter, a convenient method of producing 4-homoisotwistane was developed by N. Takaishi et al [Synthe. Commun., 4, 225 (1974)], and further study on the reactivity and the functionalization reaction of the bridgehead position was made by N. Takaishi et al [J.C.S. Chem. Commun., 371 (1975)]. Many derivatives of that undecane have also been synthesized [K. Aigami et al, J. Med. Chem, 19, 536 (1976)].

SUMMARY OF THE INVENTION

The present inventors have examined a wide variety of 4-homoisotwistane derivatives and have succeeded in synthesizing 3-alkoxy-4-homoisotwistanes represented by the formula (I) and possessing an excellent perfume, which have never been reported in any literature. The invention bases its achievement on this finding.

DETAILED DESCRIPTION OF THE INVENTION 3-alkoxy-4-homoisotwistane of the formula (I) according to the invention is produced by reacting 3-halogeno-4-homoisotwistane of the formula (II) with an alcohol of the formula (III) as is shown by the following reaction formula:

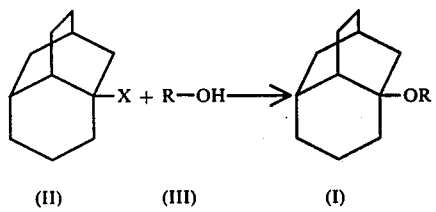

wherein X represents a chlorine or bromine atom, and R is the same as defined above.

The 3-halogeno-4-homoisotwistane of the formula (II) is dissolved in the alcohol of the formula (III), and the resulting mixture is reacted at a temperature ranging from 50° to 100° C. for 15 minutes to 5 hours to yield the desired compound of the formula (I). Suitable alcohols having the formula (III) include, for example, methanol, ethanol, n-propanol, iso-propanol, n-butanol, sec-butanol, iso-butanol, amyl alcohol, hexy alcohol, cyclopentanol and cyclohexanol. In the case where anhydrous methanol, anhydrous ethanol or anhydrous butanol is used, the mixture may preferably be refluxed at its boiling point for 0.5 to 2 hours. In the presence of silver oxide and the like as a condensing agent, the reaction proceeds more rapidly. Moreover, the 3-alkoxy-4-homoisotwistane of the formula (I) may also be produced, for instance, by reacting a 3-hydroxy-4-homoisotwistane with sodium hydride and the like, and reacting the resulting alkoxide with the corresponding alkyl halide.

The structure of the present compound of the formula (I) thus obtained has been confirmed by the results of the elemental analyses and various spectral data; that is, determination of the molecular formula results from the elemental analyses and mass spectra, and the existence of the ether bond (~1100 cm$^{-1}$) comes from the infrared absorption spectra. Particularly, with respect to the methoxy derivative [R=CH$_3$ in the formula (I)], the characteristic absorption of —OCH$_3$ is observed at 2810 cm$^{-1}$, and with respect to the methoxy, ethoxy and n-butoxy derivatives, the characteristic absorptions of —OCH$_3$ (3.2 ppm, s), —OCH$_2$CH$_3$ (3.4 ppm, q, 1.2 ppm, t) and —OCH$_2$CH$_2$CH$_2$CH$_3$ (3.3 ppm, t, 0.9 ppm, t) are observed in the $^1$HNMR spectra. The fact that an alkoxy group is bound to the bridgehead atom is ascertainable by the singlet absorptions at 75.3, 75.2 and 74.9 ppm in the $^{13}$CNMR spectra. The existence of the carbon skeleton of the 4-homoisotwistane according to this invention is supported by the fact that seven absorption lines at a high magnetic field of the $^{13}$CNMR spectrum observed with the 3-hydroxy-4-homoisotwistane synthesized by Aigami et al [J. Med. Chem., 19, 536 (1976)], each peak of which is not assigned, are in excellent agreement with the methoxy, ethoxy and n-butoxy derivatives of the invention (Table 1). Three absorption lines at a low magnetic field, exclusive of the absorption lines assigned to the carbon atom, to which are bound the alkoxy and hydroxy groups, are estimated to be the absorption lines due to three carbon atoms adjacent to one carbon atom having a substituent group. The chemical shifts are changed, depending on the differences in the influence exerted by the substituted group.

The 3-alkoxy-4-homoisotwistanes according to the invention are novel compounds and possesses the same carbon skeleton as patchouli alcohol and seychellene which belong to the natural sesquiterpenes, and therefore, a novel perfume and flavor composition possessing a characteristic smell is produced by including the present compounds.

The 3-methoxy-4-homoisotwistane of the formula (I), wherein R is a methyl group, has a powerful aspic lavender odor. The 3-ethoxy-4-homoisotwistane of the formula (I), wherein R is an ethyl group, has a tomato catsup-like refreshing green odor. The 3-n-butoxy-4-homoisotwistane of the formula (I), wherein R is a n-butyl group, has a powerful borneol or camphor odor.

Therefore, the present compound may be used in the production of a perfume composition, for example, for industrial products, detergents, cleansers, aerosols for insecticides and disinfectants, and cosmetics such as soaps, lotions, bath additives ointments, milky lotions, perfumes and eau de cologne.

The invention will now be described in further detail with reference to several non-restrictive Examples.

EXAMPLE 1

3.0 Grams of 3-bromo-4-homoisotwistane (Japanese Laid-open Specification No. 51-75052) was dissolved in 30 ml of anhydrous methanol, and to the resulting solution was added 3.0 g of silver oxide. The mixture was refluxed for 30 minutes and cooled. The mixture was filtered, and the filtrate was concentrated to obtain a residue which was distilled under reduced pressure to give 2.0 g (yield, 84.8%) of 3-methoxy-4-homoisotwistane as a colorless liquid having a boiling point of 85° to 86° C./4 mmHg.

Elemental analysis: as $C_{12}H_{20}O$;

|  | C | H |
| --- | --- | --- |
| Calculated (%): | 79.94 | 11.18 |
| Found (%): | 80.1 | 11.2 |

IR (liquid film); 2810, 1110, 1090, 1060 cm$^{-1}$.
$^1$HNMR (solvent; CDCl$_3$) δ; 0.9∼2.3 (m), 3.2 (s,—C$\underline{H}_3$)
MS (relative intensity); 180 (M$^+$, 100), 152 (20), 148 (32), 111 (24), 110 (74), 109 (97), 98 (34), 91 (28), 79 (38), 67 (26).
$^{13}$CNMR (solvent; CDCl$_3$) δc (multiplicity); 19.2 (t), 20.2 (t), 25.3 (t), 25.7 (d), 30.7 (t), 31,3 (t), 32.7 (d), 33.9 (t), 35.9 (d), 39.1 (t), 48.2 (q), 75.3 (s).

EXAMPLE 2

3.0 Grams of 3-bromo-4-homoisotwistane (Japanese Laid-open Specification No. 51-75052) was dissolved in 30 ml of anhydrous ethanol, and to the resulting solution was added 3.0 g of silver oxide. After refluxing of the mixture for 30 minutes, the mixture was treated in the same manner as described in Example 1, thereby yielding 2.0 g (yield, 79.0%) of 3-ethoxy-4-homoisotwistane as a colorless liquid having a boiling point of 90° to 91° C./4 mmHg.

Elemental analysis: as $C_{13}H_{22}O$

|  | C | H |
| --- | --- | --- |
| Calculated (%): | 80.35 | 11.41 |
| Found (%): | 80.5 | 11.3 |

IR (neat) ; 1110, 1090, 1060 cm$^{-1}$.
$^1$HNMR (solvent; CDCl$_3$) δ; 1.2 (t,—C$\underline{H}_3$), 3.4 (q,—OC$\underline{H}_2$CH$_3$), 1.0 ∼2.3 (m).
MS; 194 (M$^+$, 100), 166 (21), 165 (21), 149 (24), 148 (29), 124 (63), 123 (85), 112 (28), 95 (28), 91 (27), 81 (24), 79 (41), 67 (37), 55 (28).
$^{13}$CNMR (solvent; CDCl$_3$) δc (multiplicity); 16.4 (q), 19.2 (t), 20.4 (t), 25.3 (t), 25.8 (d), 30.8 (t), 31.4 (t), 32.7 (d), 35.0 (t), 30.4 (d), 39.5 (t), 55.4 (t), 75.2 (s).

EXAMPLE 3

3.0 Grams of 3-bromo-4-homoisotwistane (Japanese Laid-open Specification No. 51-75052) was dissolved in 30 ml of anhydrous n-butanol, and to the resulting solution was added 3.0 g of silver oxide. The mixture was refluxed for 2 hours and then treated in the same manner as described in Example 1 to obtain 2.5 g (yield, 86.0%) of 3-butoxy-4-homoisotwistane having a boiling point of 93° to 94° C./1 mmHg.

Elemental analysis: as $C_{15}H_{26}O$

|  | C | H |
| --- | --- | --- |
| Calculated (%): | 81.02 | 11.79 |
| Found (%): | 81.2 | 11.6 |

Ir (neat); 1105, 1090 cm$^{-1}$;
$^1$HNMR (solvent; CDCl$_3$) δ3.3 (t,—OC$\underline{H}_2$CH$_2$—), 0.9 (t,—C$\underline{H}_3$), 0.8 ≈2.5 (m)
MS; 222 (M$^+$, 23), 149 (29), 148 (100), 133 (20), 120 (35), 119 (82), 107 (24), 106 (34), 105 (61), 94 (34), 92 (33), 91 (81), 81 (27), 80 (34), 79 (82), 78 (21), 77 (35), 67 (38), 66 (85), 56 (72).
$^{13}$CNMR (solvent CDCl$_3$) δc (multiplicity); 14.1 (q), 19.2 (t), 19.6 (t), 20.3 (t), 25.4 (t), 25.7 (d), 30.8 (t), 31.4 (t), 32.8 (d), 33.1 (t), 35.0 (t), 36.7 (d), 39.2 (t), 59.9 (t), 74.9 (s).

EXAMPLE 4

A novel composition with a green, leafy refreshing odor was produced by adding 100 g of the 3-methoxy-4-homoisotwistane to 900 g of the following perfume composition:

| Perfume Composition for Herbal Shampoo | |
| --- | --- |
| Terpinyl acetate | 130 |
| Cedar wood oil | 100 |
| Bergamot oil | 80 |
| Oak moss abs | 60 |
| Amyl salicylate | 60 |
| Coumarin | 60 |
| Galbanum resinoid | 40 |
| Musk ketone | 20 |
| Cedryl acetate | 40 |
| Citronellol | 40 |
| Geraniol | 40 |
| Lavandin oil | 40 |
| Eugenol | 30 |
| Geranyl acetate | 30 |
| Geranium oil | 30 |
| Patchouli oil | 25 |
| Neroli oil | 60 |
| Synthetic civet | 15 |
| Dipropylene glycol | 100 |
| | 1000 |

EXAMPLE 5

A novel composition with a refreshing odor was produced by adding 50 g of the 3-ethoxy-4-homoisotwistane to 950 g of the following composition:

| Perfume Composition for After-shave Lotion | |
| --- | --- |
| Galvanum oil 10% | 120 |
| Bergamot | 100 |
| p-tert-Butylcyclohexyl acetate | 100 |
| Cedryl acetate | 100 |
| Methyl, octyl, acetaldehyde 10% | 80 |
| Jasmine oil | 60 |
| Lemon oil | 60 |
| Oak moss abs 50% | 50 |
| Lavandian oil | 60 |
| Clove oil | 50 |
| Neroli oil | 50 |
| Orange oil | 40 |
| Dedecanol 10% | 30 |
| Styralyl acetate | 30 |
| Patchouli oil | 20 |
| Sandalwood oil | 10 |
| α-Isomethylionone | 10 |
| 1,1-Dimethyl-4-acetyl-6-tert-butylindane | 10 |

-continued

Perfume Composition for After-shave Lotion

| | |
|---|---|
| | 980 |

-continued

Perfume Composition for Dentifrice

| | |
|---|---|
| | 1000 |

Table 1

($^{13}$CNMR Chemical Shifts)

| Structure | | | | | | | | | | | | | | |
|---|---|---|---|---|---|---|---|---|---|---|---|---|---|---|
| 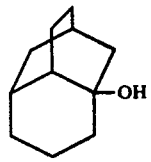—OH | 19.6 (t) | 20.3 (t) | 25.4 (t) | 26.1 (d) | 30.3 (t) | 31.4 (t) | 33.1 (d) | 40.3 (d) | 41.2 (t) | 41.7 (t) | 71.0 (s) | — | — | — |
| 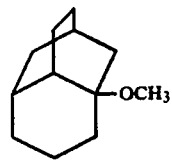—OCH$_3$ | 19.2 (t) | 20.2 (t) | 25.3 (t) | 25.7 (d) | 30.7 (t) | 31.3 (t) | 32.7 (d) | 33.9 (t) | 35.9 (d) | 39.1 (t) | 75.3 (s) | 48.2 (q) | — | — |
| 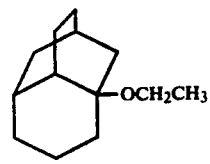—OCH$_2$CH$_3$ | 19.2 (t) | 20.4 (t) | 25.3 (t) | 25.8 (d) | 30.8 (t) | 31.4 (t) | 32.7 (d) | 35.0 (t) | 36.4 (d) | 39.5 (t) | 75.2 (s) | 55.4 (t) | 16.4 (q) | — |
| 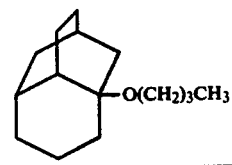—O(CH$_2$)$_3$CH$_3$ | 19.2 or 19.6 (t) | 20.3 (t) | 25.4 (t) | 25.7 (d) | 30.8 (t) | 31.4 (t) | 32.8 (d) | 33.1 or 35.0 (t) | 36.7 (d) | 39.2 (t) | 74.9 (s) | 59.9 (t) | 33.1 or 35.0 (t) | 19.2 or 19.6 (t) | 14.1 (q) |

The percentage values appearing in the above composition each show a concentration of a dipropylene glycol solution.

EXAMPLE 6

A novel composition with a sweet camphor and somewhat grassy-leafy odor was produced by adding 20 g of the 3-n-butoxy-4-homoisotwistane to 980 g of the following perfume composition:

Perfume Composition for Dentifrice

| | |
|---|---|
| Peppermint oil | 500 |
| Spearmint oil | 200 |
| L-Menthol | 200 |
| Anethole | 100 |

What is claimed as intended to be secured by Letters Patent is:

1. A 3-alkoxy-4-homoisotwistane represented by the formula (I),

(I)

wherein R represents an alkyl group having 1 to 6 carbon atoms or a cycloaklyl group having 5 to 6 carbon atoms.

2. A 3-alkoxy-4-homoisotwistane according to claim 1, wherein R in the formula (I) is an alkyl group having 1 to 4 carbon atoms.

* * * * *